(12) United States Patent
Painchaud et al.

(10) Patent No.: US 8,517,222 B2
(45) Date of Patent: Aug. 27, 2013

(54) DEVICE FOR DISPENSING A LIQUID IN A TANK

(75) Inventors: Gaetan Painchaud, Francheville (FR); Sylvain Lanzi, Chirens (FR); Xavier Julia, Villefontaine (FR)

(73) Assignee: Rexam Healthcare la Verpilliere (FR)

( * ) Notice: Subject to any disclaimer, the term of this patent is extended or adjusted under 35 U.S.C. 154(b) by 231 days.

(21) Appl. No.: 12/891,393

(22) Filed: Sep. 27, 2010

(65) Prior Publication Data

US 2011/0068133 A1 Mar. 24, 2011

Related U.S. Application Data

(63) Continuation of application No. PCT/FR2009/000357, filed on Mar. 27, 2009.

(30) Foreign Application Priority Data

Mar. 27, 2008 (FR) ...................................... 08 51994

(51) Int. Cl.
*B65D 37/00* (2006.01)

(52) U.S. Cl.
USPC ............................ 222/212; 222/420; 222/494

(58) Field of Classification Search
USPC ................. 222/420, 498, 499, 422, 511, 513, 222/514, 518, 494, 495, 496
See application file for complete search history.

(56) References Cited

U.S. PATENT DOCUMENTS

| | | | | |
|---|---|---|---|---|
| 4,739,906 A | * | 4/1988 | LoTurco | 222/212 |
| 5,226,568 A | * | 7/1993 | Newton et al. | 222/212 |
| 5,836,484 A | * | 11/1998 | Gerber | 222/494 |
| 6,334,552 B1 | * | 1/2002 | Bougamont et al. | 222/380 |
| 6,616,012 B2 | * | 9/2003 | Dark | 222/1 |
| 2004/0134940 A1 | * | 7/2004 | Hearld et al. | 222/481.5 |
| 2006/0261097 A1 | * | 11/2006 | Bailey | 222/494 |
| 2009/0218373 A1 | * | 9/2009 | Pardes et al. | 222/494 |

FOREIGN PATENT DOCUMENTS

| | | |
|---|---|---|
| JP | 2001240088 A | 9/2001 |
| JP | 2003028328 A | 1/2003 |
| WO | 2006119315 A2 | 11/2006 |

OTHER PUBLICATIONS

French Search Report; Application No. 0851994; Dec. 17, 2008; 6 pages.
International Preliminary Report on Patentability and Written Opinion of the International Searching Authority; PCT/FR2009/000357; Nov. 2, 2010; 6 pages.
International Search Report; PCT/FR2009/000357; Aug. 31, 2009; 2 pages.
English translation of JP Notice of Reasons for Rejections Application No. JP 2011-501269 Mailing Date: May 28, 2013 4 pages.

* cited by examiner

*Primary Examiner* — Kevin P Shaver
*Assistant Examiner* — Michael Melaragno
(74) *Attorney, Agent, or Firm* — St. Onge Steward Johnston & Reens LLC

(57) ABSTRACT

A device for dispensing liquid contained in a container, the device including an elastomer element that can take up: a liquid release position allowing liquid to flow out of the device; and a non-return position preventing liquid from flowing back into the device; the device further including a bearing mechanism against the elastomer element in register with a recessed zone, serving to deform the elastomer element in its non-return position.

7 Claims, 2 Drawing Sheets

DEVICE FOR DISPENSING A LIQUID IN A TANK

CROSS-REFERENCE TO RELATED APPLICATIONS

The present application is a continuation of pending International patent application PCT/FR2009/000357 filed Mar. 27, 2009, which designates the United States and claims priority from French patent application FR 0851994 filed Mar. 27, 2008, the content of which is incorporated herein by reference.

FIELD OF THE INVENTION

The present invention relates to the field of dispensing liquid that is contained in a container. More particularly, but not exclusively, the invention relates to dispensing predetermined metered quantities or "doses" of liquid, e.g. for eye, nose, or mouth use, in particular for dispensing eye drops, i.e. drops of collyrium or eyewash.

BACKGROUND OF THE INVENTION

Bottles are already known that contain a liquid such as a collyrium, and that are provided with dropper systems for dispensing the liquid in the form of drops. Often it is necessary to preserve the liquid from any risk of being contaminated by external agents such as bacteria. Simple means for keeping the liquid sterile consist in using a bottle that contains a single metered quantity only and that is to be discarded after being used for the first time. Unfortunately, the use of disposable bottles is ecologically harmful.

As an alternative to using such a single-dose bottle, it is possible to use a bottle designed to be used a plurality of times, and that can be closed again once a metered quantity has been dispensed, in order to dispense other metered quantities of liquid subsequently. The difficulty that arises when using a multi-dose bottle is how to preserve the stored liquid. Each time a metered quantity of liquid is dispensed, there is a risk that external agents might enter the container, and thereby contaminate the stored liquid. In order to make sure that the liquid is not contaminated, chemical preservatives are generally added to the liquid. Unfortunately, it has been observed that the use of such preservatives can give rise to allergies in certain users, or to undesirable side effects.

SUMMARY OF THE INVENTION

An object of the present invention is to provide a liquid dispenser device that can be used a plurality of times, and that guarantees satisfactorily that the preserved liquid is not contaminated, without it being necessary to add preservatives to the liquid.

To this end, the invention provides a device for dispensing liquid contained in a container, said device including an elastomer element that can take up:
  a liquid release position allowing liquid to flow out of the device; and
  a non-return position preventing liquid from flowing back into the device;
  said device further including bearing means bearing against the elastomer element in register with a recessed zone, serving to deform the elastomer element so that it takes up its non-return position.

Thus, it is proposed for the non-return position of the elastomer element to involve deformation of the elastomer element, so that the elastomer element seeks to revert to its initial (non-deformed) shape, thereby enabling stress to be exerted on the elastomer element, and thus enabling it to be pressed against another element, in order to provide sealing for the device when in the non-return position. As a result, once the liquid contained in the container has flowed out from a sealed zone of the device, said liquid cannot re-enter said sealed zone that is closed by the elastomer element pressed in leaktight manner against another element of the device. By means of this arrangement, the liquid contained in the container can flow in one direction only, i.e. it can only flow out of the container. In other words, the elastomer element provides dynamic sealing for the device.

It should be noted that the deformation of the elastomer element is preferably bending deformation, i.e. the bearing means exert a force locally on the elastomer element, in register with the recessed zone, in such a manner as to cause it to flex. Due to this flexing, the elastomer element seeks to revert to its initial shape, and therefore remains pressed locally against the bearing means, thereby providing the desired sealing. It should be noted that the deformation is generated by bearing on the elastomer element in register with a recessed zone, i.e. a space is provided behind that portion of the elastomer element against which a bearing force is exerted in order to enable it to be deformed, and more precisely in order to enable it to be caused to flex. This deformation therefore differs from mere compression of the elastomer element against a hard surface. Thus, in addition to possible general compression of the elastomer element, the bearing means generate local deformation that changes the general shape of the elastomer element.

Among the advantages of the device, it can be understood that it is usable on multi-dose containers and guarantees, at least in part, non-contamination of the liquid stored in the container. Advantageously, the liquid is free of any preservatives, since the sealing procured by the elastomer element is sufficient to prevent it from being contaminated. Naturally, it is also possible to make provision for the liquid to contain preservatives.

The sealing proposed by the device is advantageous because it does not put any constraint on the user. For example, it differs from using a filter membrane, provided with a filter, and designed to prevent dirt from penetrating into the container. Although advantageous for preventing the container from being contaminated, such a filter membrane constitutes a brake to delivery of metered quantities of liquid, which is uncomfortable for the user who must apply greater force to the device in order to dispense liquid. Preferably, the device presented above does not suffer from such braking on dose delivery, since the release position can allow liquid to flow past without braking it to any particular extent.

It should be noted that the elastomer element may be made of rubber, of silicone, of thermoplastic elastomer (TPE), or of any other material suitable for providing sealing.

In the description below, the "downward" direction designates the direction towards the liquid container of the device, and the "upward" direction designates the opposite direction.

The dispenser device may also have one or more of the following characteristics.

The elastomer element in its liquid release position is subjected to deformation corresponding to an amplification of the deformation to which it is subjected in its non-return position. Thus, the elastomer element takes up its release position only once it has been subjected to pressure sufficient to deform it to a greater extent, such as the pressure exerted by a user on the container in order to cause the fluid to flow out, so that it is not possible for the elastomer element to take up this liquid release position without the pressure applied by the user. Such a configuration of the elastomer element guarantees good dynamic sealing, allowing the liquid to pass through in one direction only.

The bearing means comprise first bearings means and second bearing means that are disposed in staggered manner and that bear respectively against a first face and against a second face of the elastomer element, said second face being opposite from the first face. Thus, the first and second bearing means bear against the elastomer element in opposite directions. For example, the first bearing means are central bearing means bearing against the center of one face of the elastomer element, and the second means are concentric bearing means bearing against an opposite face of the elastomer element, around the central bearing means and in a direction opposite from the bearing direction of the central bearing means. The combination of the first and second bearing means makes it possible to cause the elastomer element to flex, so that it is pressed by the first bearing means against the second bearing means, or vice versa, thereby providing the sealing.

The elastomer element is fitted around an inner core of the device. Thus, said core can carry bearing means such as a projection, locally deforming the elastomer element, in such manner as to press it in leaktight manner against the bearing means.

The bearing means comprise a projection formed on an inner core of the device, on which core the elastomer element is mounted. For example, this projection comprises a circular rib.

The bearing means comprise a projection provided on a casing covering the elastomer element. For example, this projection comprises a central rib, and more precisely one or more studs disposed in the center of the casing.

The bearing means comprise a projection provided on the elastomer element, and preferably made in one piece with said elastomer element.

The elastomer element comprises a dish-shaped disk that is curved downwards, or a cone that is curved downwards, and is preferably received in a funnel-shape formed in an inner core of the device.

The elastomer element comprises a cone that is curved upwards, and that is preferably fitted over an inner core of the device.

The device includes a liquid guide channel that guides the liquid released by the elastomer element out of the device.

The elastomer element is provided with metering means for metering out the liquid to be dispensed. For example, these metering means define a cavity having a geometrical shape making it possible to form drops of liquid that are calibrated so that they always have the same volume. It is particularly advantageous to incorporate these metering means directly into the elastomer element, since the liquid that is released by the elastomer element in the release position, and that thus flows out of the sealed zone, then flows inside the elastomer element only. As a result, the risks of liquid penetrating into other portions of the device after it is released are reduced. When the metering means are provided on a part other than the elastomer element, e.g. on a casing covering the elastomer element, the liquid can penetrate into other parts of the device while it is flowing between the elastomer element and the metering means. In addition, by incorporating the metering means into the elastomer element, it is possible to reduce a dead volume that might contain contaminated liquid, corresponding to the volume situated between the sealed zone and the metering means, and defined in this example by the elastomer element. The elastomer element is flexible and can have a shape that fits snugly against the parts and reduces the dead volume to as small a volume as possible, this reduction being easier to achieve than when the dead volume is defined by rigid parts.

BRIEF DESCRIPTION OF THE DRAWINGS

The invention can be better understood on reading the following description given merely by way of example, and with reference to the accompanying drawings, in which:

FIG. 1b is a diagrammatic section view of the elastomer element of FIG. 1a, the non-deformed configuration of the element being shown in dashed lines;

FIG. 1c is an exploded perspective view of an inner core and of the non-deformed elastomer element of the device of FIG. 1a, and a view in section and in perspective of a casing of the device of FIG. 1a;

FIG. 2b is a view similar to FIG. 1b, showing the elastomer element of the device of FIG. 2a;

FIG. 3a is a view similar to FIG. 1a, showing a second embodiment;

FIG. 3b is a view similar to FIG. 1b, showing the elastomer element of the FIG. 3a device; and FIG. 3c is an exploded perspective view of a core of the device of FIG. 3a, a cutaway perspective view of the elastomer element of the device of FIG. 3a, and a view in section and in perspective of a casing of the device of FIG. 3a.

DETAILED DESCRIPTION OF THE INVENTION

Figure 1A:
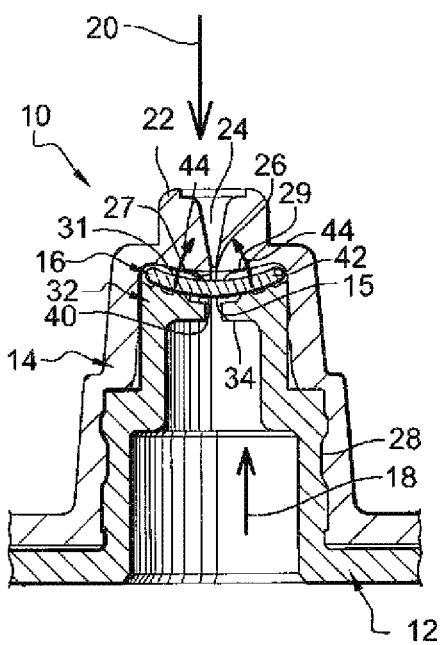
FIG. 1a is a diagrammatic section view of a first embodiment of a dispenser device of the invention, including an elastomer element shown in the non-return position.

As can be seen in FIG. 1a, a first embodiment of a dispenser device 10 includes an inner core 12 that is designed to be mounted on a container (not shown) containing a liquid that is dispensed by the device 10. For example, the liquid is eyewash or collyrium. The device 10 further includes an outer casing 14 that may optionally be covered by a protective cap (not shown). Between the core 12 and the casing 14, there is interposed an elastomer element 16, e.g. a member made of silicone, of rubber, or indeed of TPE, having a "top" first face 13, and an opposite "bottom" second face 15. This elastomer element 16 provides dynamic sealing in the device 10, i.e. it allows liquid to flow from the container towards the outside of the device, in the direction indicated by arrow 18, but it prevents liquid from flowing from the outside of the device towards the inside of the device, i.e. in the direction indicted by arrow 20.

The outer casing 14 has a "release" end 22 in which a "release" orifice is formed for releasing liquid from the device 10. Immediately upstream from said orifice 22, the casing 14 is provided with metering means 24 for metering out liquid to be dispensed. Said metering means 24 comprise a cavity, the volume of which makes it possible to meter out the quantity of liquid to be dispensed each time the device is used, i.e. when the user applies a certain amount pressure to the container by squeezing it. In addition, the cavity of the metering means 24 has a special shape that enables a drop-shape to be imparted to the metered quantity of liquid that is dispensed. Upstream from the metering means 24, the casing 14 is provided with a dispensing orifice 26 that opens out onto an inside surface 25 of the end 22 of the casing. In the vicinity of the outlet orifice 26, said surface 25 is provided with projections 27 serving as first bearing means bearing against the first face 13 of the elastomer element 16. More precisely, the first bearing means 27 comprise four holding studs, separated from each other by four channels 29, formed in the inside wall 25, and serving to guide liquid released by the elastomer element, as described below. The channels 29 are spaced apart at 90° from one another, so that, in this example, they are aligned in pairs. Thus, in FIG. 1a, the section of the figure passes through the center of two aligned channels 29. As can be seen in FIG. 1a, the projections 27 formed in the inside wall 25 of the casing define a first recessed zone or recess 31, constituting a space between a portion of the elastomer element 16 and the casing 14. The casing 14 is further provided with means 28 for assembling it to the inner core 12. More precisely, the means 28 comprise a shape that can provide tight snap-fastening, e.g. a projection 28 that is designed to co-operate with complementary means 30 provided in the core 12, e.g. a collar 30 shown in FIG. 1c. The assembly means 28, 30 may take other forms, and the casing 14 and the core 12 may also be secured together by clamping or by ultrasound welding.

In this example, the inner core 12 has a hollow cylinder shape, having an orifice 34 at its end 32 for the purpose of releasing liquid from the core. The end 32 of the inner core 12 is provided with a bearing zone bearing against the elastomer element 16. More precisely, said bearing zone comprises two circular projections 36, 38 serving as second bearing means, and designed to bear against the second face 15 of the elastomer element 16. The bearing means 36, 38 are disposed in staggered manner relative to the bearing means 27, i.e. they are not disposed in register with the means 27. At its center, the surface 32 is also provided with a recessed zone or recess 40, into which the orifice 34 opens out.

Figure 1C:
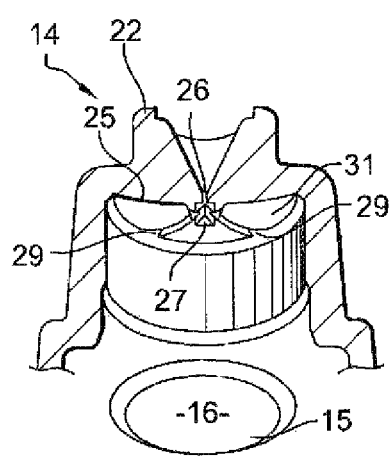
Figure 1C:
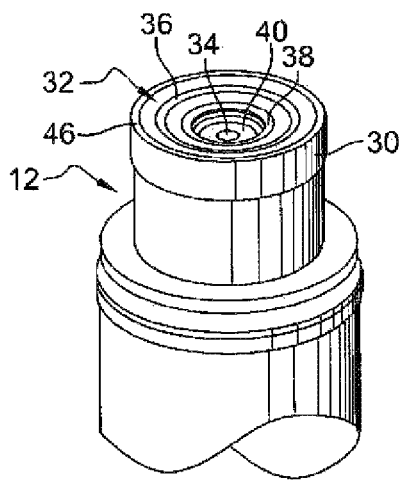

As can be seen in FIG. 1c, the elastomer element 16 is in the shape of a dish-shaped disk. When the elastomer element 16 is in the initial position, i.e. when it is not deformed, it has the shape shown in dashed lines in FIG. 1b or in FIG. 1c, curved upwards. In addition to this non-deformed position, the elastomer element 16 can take up two other positions, namely a non-return or "check" position, shown in FIG. 1a and in solid lines in FIG. 1b, and in which its general shape is the shape of a downwardly-curved disk, and a liquid release position in which the shape of the element 16 is curved downwards to a greater extent, the periphery 42 of the element 16 then being moved upwards, as indicted by the arrows 44, in order to allow liquid to pass between the projections 36, 38 of said peripheral portion 42.

The inner core 12 and the outer casing 14 are preferably made of a plastics material, e.g. of polypropylene or of polyethylene.

Assembly of the device 10 is described below with reference to FIG. 1c. Firstly, the elements 12, 14, and 16 are manufactured separately. Then the elastomer element 16, in its non-deformed initial position, is positioned on the surface 32 of the core 12, by centering means 46 provided at the end 32. Once the elastomer element 16 is positioned on the core 12, the outer casing 14 is mounted over it, in such a manner as to cause the assembly means 28, 30 to co-operate. Assembly of the core 12 and of the casing 14 deforms the elastomer element 16 that therefore takes up its non-return position as can be seen in FIG. 1a. In this non-return position, the first bearing means 27 that are arranged in register with the recessed zone 40 of the core 12 deform the elastomer element, and more precisely bear on the center of the elastomer element 16 so as to cause it to flex downwards, into the recess 40. In parallel, the second bearing means 36, 38 that are arranged in register with the recesses 31 deform the elastomer element by bearing on its peripheral portion 42, so that, with the means 27, the element 16 flexes and its concavity reverses, as shown in solid lines in FIG. 1b, so that it is pressed by the first means 27 against the second means 36, 38, thereby providing sealing.

Operation of the device 10 is described below. When the device is in the rest position, the user does not exert any pressure on the container, so that the liquid contained in the container remains inside said container. In this position that can be seen in FIG. 1a, and as described above, the element 16 is in the non-return position, the bearing means 27, 36, 38 deforming it by pressing it against the projections 36, 38, so as to prevent liquid from penetrating into the container, and more particularly into the outlet orifice 40.

In said non-return position, the bearing means 36, 38 against which the peripheral portion 42 of the element 16 is pressed close a zone referred to as the "sealed zone", into which impurities such as bacteria cannot penetrate, or, at least, can penetrate to a very small extent only, without that being problematic as regards satisfying the constraints of preserving the liquid contained in the device 10. In this example, the sealed zone comprises the internal volume of the container, the internal volume of the core 12, the orifice 34, and the recess 40.

When the user exerts pressure on the container by squeezing it, liquid, possibly preceded by air, exerts pressure on the elastomer element 16 that deforms to a further extent in the direction indicated by the arrows 44, so that liquid can flow into the space situated between the projections 36, 38 and the bottom face 15 of the elastomer element 16. The liquid released in this way flows around the elastomer element, by flowing past the edge of its periphery 42, and then penetrates between its top face 13 and the surface 25 of the casing 14. More precisely, the liquid penetrates into the channels 29, and then between the studs 27, and then flows out via the release orifice 26, in order to fill the metering means 24. Once the metering means 24 are full, a drop of liquid can form and be released from the device 10. When the user ceases to exert pressure, the liquid contained in the container no longer exerts pressure on the elastomer element 16, so that said elastomer element is no longer constrained to deform and thus to remain in its liquid release position, and it therefore resumes its non-return position, in which the peripheral portion 42 bears against the projections 36, 38.

It should be noted that the device in FIGS. 1a to 1c is particularly advantageous because the element 16 is sandwiched between the core 12 and the casing 14, and very little space is provided between the elastomer 16 and the inside surface of the casing 14. As a result, little space is left inside the device for enabling any liquid that has passed through the orifice 26 and that might contaminate the inside of the device to pass back through the opening 26 in the opposite direction indicated by the arrow 20.

Figure 2A:
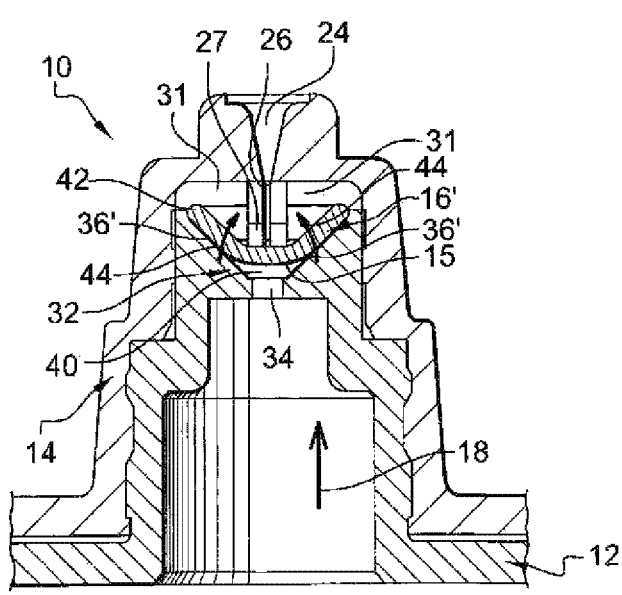
FIG. 2a is a view similar to the FIG. 1a view, showing a variant embodiment of a device.
Figure 2B:
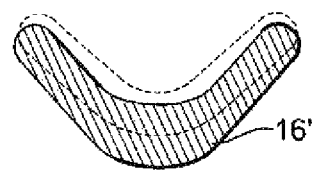

In a variant embodiment shown in FIGS. 2a, 2b, the elastomer element 16' is in the general shape of a downwardly-curved cone. In addition, at its end 32, the inner core 12 has a funnel shape extending the release orifice 34, this funnel shape having a bearing surface 36' serving as second bearing means bearing against the elastomer element 16', and more precisely bearing against the peripheral portion 42 of said element 16'.

In this variant, the outer casing 14 is not necessarily provided with guide channels for guiding the liquid 29 towards the orifice 26, the top surface 13 of the elastomer element 16' being curved sufficiently to guide the liquid towards the bottom end of the orifice 26.

It should be noted that the bearing surfaces 36' may optionally be provided with projections such as the ribs 36, 38 of FIG. 1c.

The method of assembling the device 10 of FIG. 2a is analogous the method of assembly shown in FIG. 1c. In this variant, the funnel-shaped walls of the end 32 act as centering means 46, so that, before the outer casing 14 is mounted, the elastomer element 16' in its non-deformed position (shown in dashed lines in FIG. 2b) is easy to position on the inner core 12. When the outer casing 14 is mounted on the core 12 provided with the elastomer element 16', the first bearing means 27 deform the elastomer element 16', in a manner such that it takes up the position shown in FIG. 2a, namely the non-return position. In this position, due to the peripheral wall 42 of the elastomer element 16' being resiliently urged back against the bearing surfaces 36', liquid cannot penetrate into the sealed zone of the device 10.

It can be understood that the device 10 of FIG. 2a operates analogously to the device of FIG. 1a.

It should be noted that, in the device of FIGS. 2a, 2b, the bearing means 27 project to a greater extent than do the abutment means 27 of FIGS. 1a to 1c, and that the recess 40 extending the orifice 34 has a relatively large height that is greater than the height of the recess 40 in FIG. 1a. As a result, the elastomer element 16' of FIG. 2a is relatively remote from the orifice 34, and there is therefore no risk of it blocking said orifice 34, even when the dimensions of the element 12 or 14 vary due to manufacturing tolerances.

Figures 3A, 3B, 3C:
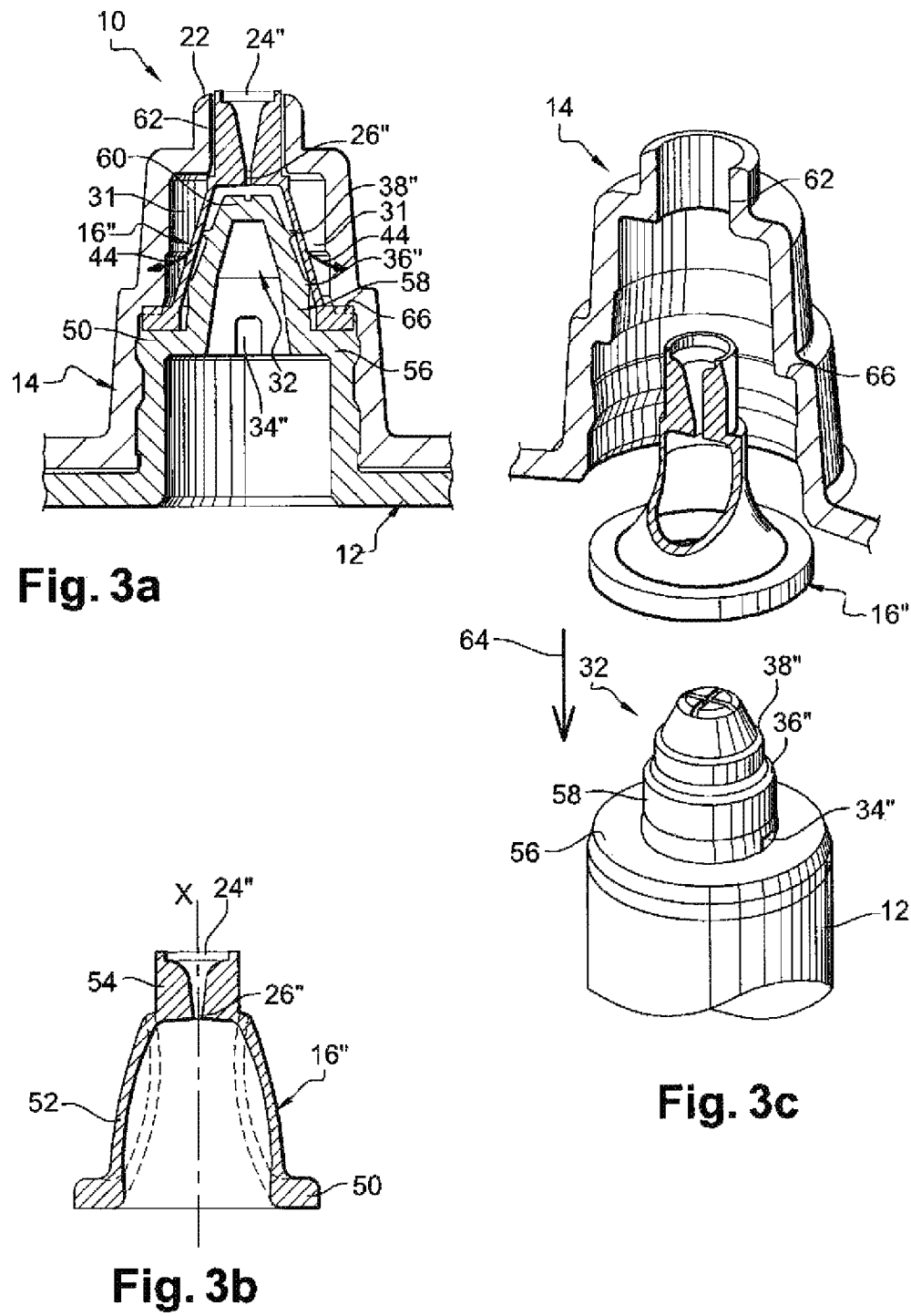

In the embodiment shown in FIGS. 3a to 3c, the elastomer element 16" is in the general shape of an upwardly-curved cone that can be likened to the shape of a teepee. In addition, the end 32 of the inner cone 12 has a general shape that can be likened to an upwardly curved cone, and more particularly the general shape of a bullet, over which the elastomer element 16" is designed to be fitted.

More precisely, the elastomer element 16" is provided with a bottom collar 50, a side wall 52 that is in the general shape of a hyperboloid, when the element 16" is in its non-deformed position, and curved towards the axis X of the element 16" (shown in dashed lines in FIG. 3b), and an end 54 that extends the wall 52, and in which means 24" for metering the liquid to be dispensed are formed. It should be noted that, in order to fit the elastomer element 16" over the core 12, said element must be made of a relatively flexible material, and the wall 52 must be relatively thin.

In addition, the end 32 of the core 12 that is designed to be covered by the elastomer element 16" is provided with a peripheral bottom base 56 serving as a base for a side wall 58 that bulges outwards, this wall 58 being provided with a top 60. The side wall 58 carries two circular projections 36", 38", similar to the ribs 36, 38 of FIG. 1c, and serving as bearing means bearing against the side wall 52 of the elastomer element. In addition, in the vicinity of the base 56, the side wall 58 is provided with two diametrically opposite cavities 34" that serve as orifices for releasing the liquid from the core 12.

The casing 14 of FIG. 3a is slightly different from the casing of FIG. 1a. This casing is not provided with metering means 24, since the metering means 24" are provided directly on the elastomer 16". Thus, the end 22 of the casing 14 defines a tubular cavity 62, leaving room for the end 54 of the elastomer element.

Assembly of the device of FIG. 3a is analogous to assembly of the devices of the preceding figures. Firstly, the elastomer element 16" is mounted over the core 12, by fitting it over the end 32 in the direction indicated by arrow 64. By mounting the element 16" over the inner core 12, its side wall 52 is caused to deform. Since, in its non-deformed position, the elastomer element 16" has a diameter less than the outside diameter of the end 32, said elastomer element is deformed by said end 32. Thus, somewhat like a sock, the element 16" deforms and thus takes up a final position corresponding to the non-return position shown in FIG. 3a. In particular, the bearing means 36", 38" exert a pressure on the side wall 52 of the elastomer element 16", so as to deform it. Once the element 16" is disposed over the core 12, it is possible to mount the outer casing 14, by assembling it in the same way as in FIG. 1a or 2a over the core 12.

It should be noted that, in this embodiment, a shoulder 66 provided on the inside of the outer casing 14 makes it possible to clamp the bottom collar 50 of the elastomer element 16" against the base 56 of the core 12. This clamping makes it possible to fasten the elastomer element 16" around the end 32, and thereby to provide static sealing between the core 12 and the casing 14. By means of this static sealing, the elastomer element 16" prevents any liquid that flows out of the cavities 34" and between the outside surface of the end 32 and the inside surface of the elastomer element 16" from penetrating between the core 12 and the casing 14. In order to achieve this static sealing, the portion 50 of the elastomer element 16" takes up a single sealing position throughout use of the device 10. It should be noted that the static sealing differs from the dynamic sealing provided by the side wall 52 of the elastomer element 16", and allowing liquid to be released in one direction.

Operation of the device of FIG. 3a is described below. This mode of operation is analogous to the mode of operation shown in the preceding figures. When the device 10 is at rest, i.e. when the user is not squeezing the container, the elastomer element 16" is in the non-return position, shown in FIG. 3a, so as to prevent liquid from penetrating into the sealed zone. In this position, the side wall 52, as deformed in particular by the bearing means 36", 38", is pressed against said bearing means, so as to prevent liquid from returning. When the user squeezes the container, liquid flows out from the core 12 via the release orifices 34". The pressure exerted by the liquid deforms the side wall 52 of the elastomer element 16" to a further extent in the direction indicated by the arrows 44 in FIG. 3a, so that a space is formed between the bearing means 36", 38" and the side wall 52, so that liquid can pass through. The liquid released in this way can then flow through the orifice 26" and into the metering means 24". Once a sufficient quantity of liquid fills the metering means 24", the liquid is dispensed from the device 10. Once the user ceases to exert pressure on the container, the liquid ceases to exert pressure on the side wall 52 of the elastomer element, so that said element is pressed, once again, against the bearing means 36", 38", and thus resumes its non-return position.

It should be noted that the invention is not limited to the above-described embodiments. In particular, the bearing means can take a multitude of forms, e.g. they can be in the form of bearing studs, such as the studs 27, in the form of circular bearing ribs, such as the ribs 36, 38, 36", 38", or indeed in the form of relatively large bearing surfaces, such as the bearing surface 36'. These bearing means may be interchanged or combined on any one of the above-described devices. In addition, it is possible to form bearing ribs directly on the elastomer element 16, 16' or 16". For example, it is possible to replace the ribs 36, 38 of FIG. 1a with a plane surface, and to provide circular ribs, similar to the ribs 36, 38, on the bottom surface 15 of the elastomer element 16, by forming them in one piece with said element 16. It is possible to make similar provisions in the devices of the other figures.

As regards assembly of the device 10, it is possible to make provision for the first step, in which the elastomer element 16, 16', 16" is mounted on the core 12, to be replaced with a step in which the elastomer element 16, 16', 16" is mounted inside the casing 14, which casing can be placed upside down so as to hold the elastomer element in position.

It is also possible to consider reducing the number of parts of the devices and the number of assembly steps, by forming the elastomer element 16, 16', 16" by overmolding or by bi-injection molding, directly in the casing 14 or on the core 12.

In addition, the device 10 may be mounted directly on a container or else on a container that is provided with a pump for dispensing the liquid. It is also possible to make provision for the container to be made in one piece with the core 12.

The advantages of the device 10 are presented above. It should be noted, in particular, that the presence of a recessed zone 31, 40 in register with the bearing means leaves a setback allowing the elastomer element 16, 16', 16" to deform so that it can take up its non-return position or its release position. Thus, the deformation of the elastomer element enables it to be caused to flex, and differs from mere compression against a surface.

What is claimed is:

1. A device for dispensing liquid contained in a container, wherein said device includes an elastomer element that can take up:
   - a liquid release position allowing liquid to flow out of the device; and
   - a non-return position preventing liquid from flowing back into the device;
   - said device further including bearing means bearing against the elastomer element in register with a recessed zone, serving to deform the elastomer element so that it takes up its non-return position, wherein the elastomer element is fitted around an inner core of the device, wherein at least a portion of the elastomer element comprises a cone sidewall that is curved upwards when the elastomer element is in a non-deformed position, and wherein the bearing means comprise a projection formed on the inner core on which the elastomer element is mounted, the projection forming a circumferential seal with the cone sidewall in the non-deformed position.

2. A device according to claim 1, wherein the elastomer element in its liquid release position is subjected to deformation corresponding to an amplification of the deformation to which it is subjected in its non-return position.

3. A device according to claim 1, wherein the bearing means comprise first bearings means and second bearing means that are disposed in staggered manner and that bear respectively against a first face and against a second face of the elastomer element, said second face being opposite from the first face.

4. A device according to claim 1, including a liquid guide channel that guides the liquid released by the elastomer element out of the device.

5. A device according to claim 1, wherein the elastomer element is provided with metering means for metering out the liquid to be dispensed.

6. The device according to claim 3, wherein the first bearing means are central bearing means bearing against the center of one face of the elastomer element, and the second means are concentric bearing means bearing against an opposite face of the elastomer element, around the central bearing means and in a direction opposite from the bearing direction of the central bearing means.

7. The device according to claim 1, wherein the device includes a metering element metering out the liquid to be dispensed.

* * * * *